(12) United States Patent
Stauffer

(10) Patent No.: US 6,852,896 B2
(45) Date of Patent: Feb. 8, 2005

(54) CONCERTED PROCESS FOR THE PRODUCTION OF AN ALKENYL SUBSTITUTED AROMATIC COMPOUND

(76) Inventor: John E. Stauffer, 6 Pecksland Rd., Greenwich, CT (US) 06831

( * ) Notice: Subject to any disclaimer, the term of this patent is extended or adjusted under 35 U.S.C. 154(b) by 209 days.

(21) Appl. No.: 10/268,803

(22) Filed: Oct. 11, 2002

(65) Prior Publication Data
US 2004/0073067 A1 Apr. 15, 2004

(51) Int. Cl.$^7$ ................................. C07C 1/20
(52) U.S. Cl. ................ 585/319; 585/469; 585/435
(58) Field of Search ............... 585/319, 469, 585/435

(56) References Cited

U.S. PATENT DOCUMENTS 3,148,222 A * 9/1964 Malone, III et al. ........ 570/203

* cited by examiner

Primary Examiner—Thuan Dinh Dang
(74) Attorney, Agent, or Firm—Patton Boggs LLP

(57) ABSTRACT

An integrated process of preparing a $C_{2-5}$ alkenyl-substituted aromatic compound using a $C_{6-12}$ aromatic compound and a $C_{2-5}$ alkane as raw materials. The process involves two reaction steps operating in tandem, the first reaction step reacts the $C_{6-12}$ aromatic compound with hydrogen chloride and molecular oxygen in the presence of a catalyst to yield water and mono-, di-, tri-, and higher chlorinated aromatic adducts. The chlorinated compounds from the first reaction step are reacted with ethane in the second reaction step to produce alkane-substituted aromatic compounds which spontaneously dehydrogenate to an alkenyl-substituted aromatic compound and hydrogen chloride. After separating the alkenyl-substituted aromatic product from the hydrogen chloride, the hydrogen chloride is recycled to the first reaction step so that there is no net production or consumption of hydrogen chloride.

38 Claims, 1 Drawing Sheet

CONCERTED PROCESS FOR THE PRODUCTION OF AN ALKENYL SUBSTITUTED AROMATIC COMPOUND

BACKGROUND OF THE INVENTION

1. Field of the Invention

This invention relates to a process of preparing an alkenyl-substituted aromatic compound from an aromatic compound and an alkane. More particularly, the present invention relates to a process of producing styrene, where benzene, hydrogen chloride and oxygen are reacted in the presence of a catalyst to yield reaction products comprising chlorinated benzene and water, and wherein the chlorinated benzene is reacted with ethane to produce styrene and hydrogen chloride.

2. Description of the Background

Alkenyl-substituted aromatic compounds, such as styrene and α-methylstyrene, are used in the production of thermoplastic polymers, such as, polystyrenes, acrylonitrile-butadiene-styrene copolymers (ABS), styrene-acrylonitrile resins (SAN), styrene-butadiene elastomeric copolymers (SBR), and formulations for unsaturated polyester resins. Divinylbenzene is also used as a polymerization monomer for special synthetic rubbers.

Styrene is generally prepared by the adiabatic or isothermic catalytic dehydrogenation of ethylbenzene in the presence of catalysts selected from metal oxides or their mixtures. Ethylbenzene is prepared by the alkylation of benzene, available as a refinery product, with ethylene coming from the cracking or dehydrogenation of ethane. Ethylene is typically derived from the thermal or steam cracking of saturated hydrocarbons rich in natural gas, ethane, propane, and butanes, or from the cracking of naptha. The alkylation reaction can be carried out in the vapor phase, using zeolite catalysts with high $SiO_2/Al_2O_3$ ratios, for example zeolites of the type ZSM-5 or Lewis acids, or in liquid phase. Alternatively, ethylbenzene can be produced from a dilute ethylene stream in a mixed phase reactor, as disclosed by ABB Lummus Global and CDTech in U.S. Pat. No. 5,756,872.

The traditional methods for the production of styrene generally require the availability of ethylene for the preparation of ethylbenzene. The conventional method of preparing styrene possesses disadvantages in several regards. The crackers used to prepare ethylene are highly costly to construct and maintain, and their operation is energy intensive. In addition, the styrene production facility must be located at the site of the cracker, because the transportation of ethylene is too expensive. Finally, the ethylene needed for the alkylation step is required to be essentially pure, otherwise undesirable alkylated products are produced and the lifetime of the alkylation catalyst is significantly reduced. Since ethane cracking produces a variety of products in addition to ethylene including, for example, propylene, acetylene, $C_4$ saturated and unsaturated hydrocarbons, and $C_5$ and $C_9$ or higher hydrocarbons, the effluent from the cracker must be separated, for example, by extractive distillation and/or selective hydrogenation, to obtain pure ethylene. These separations significantly increase the cost of producing ethylene.

The more recent technology of using dilute ethylene streams derived from off-gases from fluid catalytic cracker operations possess similar disadvantages to those mentioned above. The requirement of a suitable ethylene stream accounts for about 40 percent of the raw material cost of ethylbenzene.

An alternative process to cracking generates ethylene from the dehydrogenation of ethane, as disclosed in U.S. Pat. No. 5,430,211 and EP-B1-0,637,578. These processes rely on selective catalysts, such as platinum and/or gallium to produce clean, dilute streams of ethylene in ethane. Dilute ethylene streams produced from these dehydrogenation processes are known to successfully alkylate benzene to ethylbenzene, as disclosed, for example, in U.S. Pat. No. 5,430,211 of The Dow Chemical Company.

SUMMARY OF THE INVENTION

With the aim of simplifying traditional production processes, the Applicant has now found a new method for the preparation of alkenyl-substituted aromatic compounds in which hydrochloric acid and alkenyl-substituted aromatic compounds are produced in the same alkylation-dehydrogenation reaction.

In one embodiment of the invention, two reaction steps are operated in tandem to provide a largely self-contained process for producing alkenyl-substituted aromatic compounds from aromatic compounds, alkanes, and molecular oxygen. A first reaction step consists of the oxychlorination of the aromatic compound, for example benzene, whereby the benzene is reacted with hydrogen chloride gas and molecular oxygen in the presence of a catalyst to produce water and chlorinated benzene. The intermediate product, namely, chlorinated benzene, may consist of chlorobenzene (monochlorobenzene), dichlorobenzene, lesser quantities of trichlorobenzene and tetrachlorobenzene, and traces of pentachlorobenzene and hexachlorobenzene. A second reaction step is used to react chlorinated benzene from the first reaction step with ethane to form styrene and hydrogen chloride. The reaction may also co-produce divinylbenzene. This second reaction step is carried out in the vapor phase at elevated temperatures. Some benzene may be formed, depending on the stoichimetry of the reaction, that is, the ratio of chlorobenzene to dichlorobenzene in the feed. The unreacted benzene is returned to the first reaction step. Hydrogen chloride is also recycled from the second reaction step to the first reaction step. In this manner there is no net production nor consumption of hydrogen chloride. The process is entirely free from any dependence on a secondary or alternative chlorine source.

DETAILED DESCRIPTION OF THE INVENTION

Figure 1:
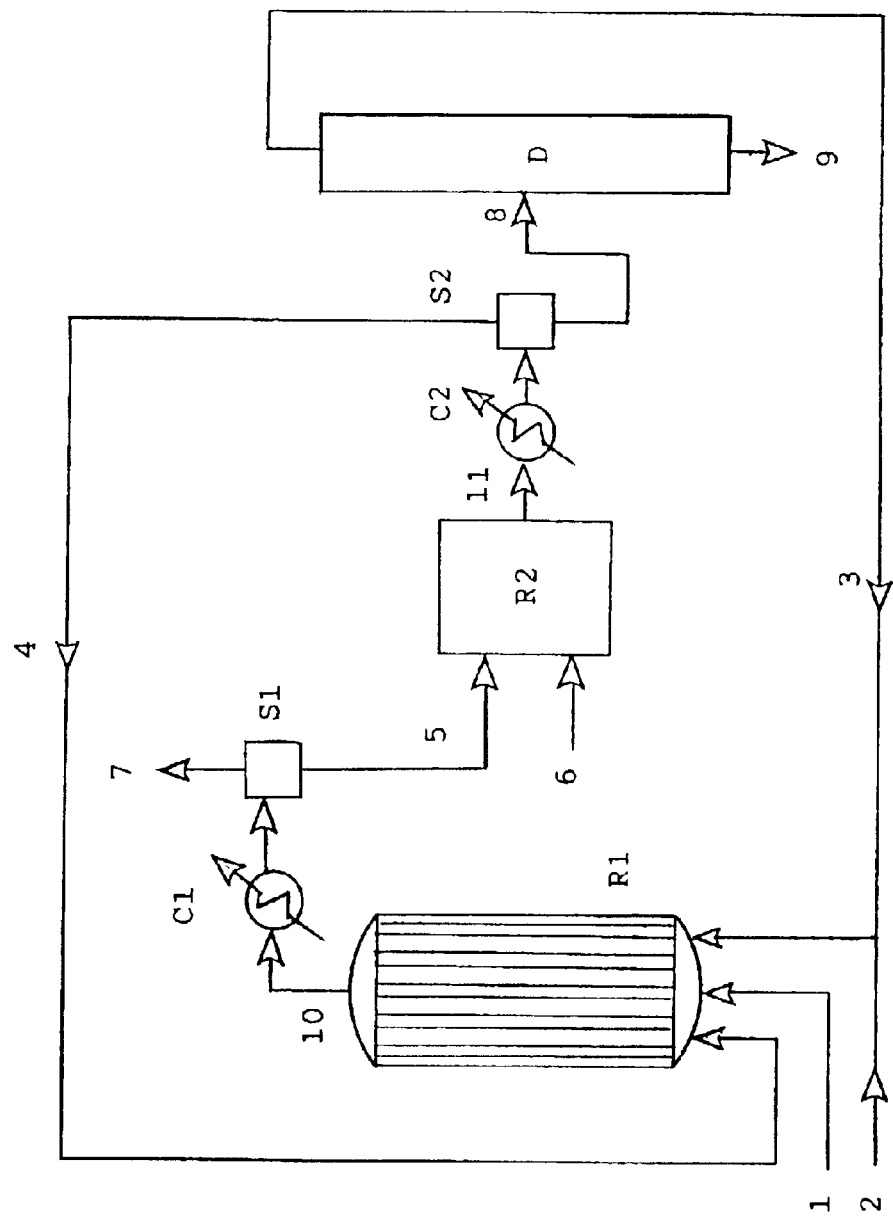
FIG. 1 is a block diagram detailing the presently disclosed process.

The present invention discloses a process for producing alkenyl-substituted aromatic compounds from a $C_{6-12}$ aromatic compound and a $C_{2-5}$ alkane, and molecular oxygen ($O_2$). Air may be substituted for pure oxygen in the process without suffering any significant loss in yield or purity. The process more specifically comprises a first reaction step wherein the $C_{6-12}$ aromatic compound, oxygen, and hydrogen chloride are reacted in the presence of a catalyst to give the reaction products —water and various chlorinated aromatic compounds consisting of mono-, di-, tri-, and higher substituted chlorinated moieties. The individual chlorinated species appear in increasingly higher concentrations inversely proportional to the number of chlorinated substitutions to the aromatic portion of the compound. For example, when the aromatic reactant is benzene ($C_6H_6$) the products would include the compounds chlorobenzene ($C_6H_5Cl$), dichlorobenzene ($C_6H_4Cl$) and lesser quantities of more highly substituted benzenes. After completion of the first reaction step, water is removed and the chlorinated aromatic compound is reacted with a $C_{2-5}$ alkane in a second reaction step to produce styrene plus hydrogen chloride. Depending on the ratio of mono- to di-substituted aromatic compounds used in the reaction feed, the initial aromatic compound from step 1 is reproduced. The alkenyl-substituted aromatic compound is separated from the hydrogen chloride along with any of the aromatic starting material which is returned to the first reaction step.

In the special case where benzene is used as the aromatic starting material and dichlorobenzene is the only chlorinated benzene produced in the first reaction step, the reactions that occur in the process can be represented by equations:

$$C_6H_6 + 2HCl + O_2 \rightarrow C_6H_4Cl_2 + 2 H_2O \qquad 1.$$

$$C_6H_4Cl_2 + C_2H_6 \rightarrow C_6H_5C_2H_3 + 2HCl \qquad 2.$$

Equation 1 above describes the reaction in the first reaction step, and equation 2 gives the reaction in the second step. By combining these two equations the following relationship is obtained which represents the overall process of the invention, shown below as equation 3:

$$C_6H_6 + C_2H_6 + O_2 \rightarrow C_6H_5C_2H_3 + 2H_2O \qquad 3.$$

Normally there would be some chlorobenzene produced in the first reaction step. The formation of this intermediate in the first reaction step and its conversion in the second reaction step can be represented, respectively by the following equations:

$$2C_6H_6 + 2HCl + O_2 \rightarrow 2C_6H_5Cl + 2H_2O \qquad 4.$$

$$2C_6H_5Cl + C_2H_6 \rightarrow C_6H_5C_2H_3 + C_6H_6 + 2HCl \qquad 5.$$

Again, by combining equations 4 and 5, the net result is the same as shown by equation 3. In this case where trichlorobenzene ($C_6H_3Cl_3$) is formed in the first reaction step, this compound may react with chlorobenzene and ethane in the second reaction step to produce styrene and hydrogen chloride according to equation 6:

$$C_6H_3Cl_3 + C_6H_5Cl + 2C_2H_6 43\ 2C_6H_5C_2H_3 30\ 4HCl \qquad 6.$$

In this balanced reaction, benzene is not formed and need not be recycled. The first reaction of this invention, better known as the Raschig Process and illustrated by equations 1 and 4, is well known in the literature. It is disclosed in U.S. Pat. No. 1,963,761 incorporated herein by reference. The process employs the familiar Deacon catalyst, which contains a copper salt. The efficiency of this catalyst may be enhanced by the addition of various metallic halogen salts, preferably the chloride salts of potassium, cesium, iron, cobalt, nickel, manganese, chromium, cerium, and lead. However, a useful effect may be attained by the use of any other metal of groups 3–8 of the periodic table. The metal catalyst should not be limited to halogen salts and may include other anions including the metal-oxides. In the preferred embodiment, the effectiveness of the catalyst is such that acceptable reaction rates are achieved when operating the process at a temperature in the range of 200° C. to 350° C. Under these conditions high yields of alkenyl-substituted aromatic compounds are produced.

There are several practical considerations regarding the first reaction step. The reaction is exothermic so that considerable heat must be removed from the catalytic reactor in order to control the temperature. This result can be realized by employing a shell and tube design for the reactor as shown schematically in FIG. 1. Alternatively, a fluidized bed reactor or a molten salt reactor can be used.

The ratios of mono-, di-, and higher chlorine substituted aromatic compounds in the product from the first reaction step can be adjusted within limits by using an excess of aromatic starting material in the feed. In this manner, a degree of control can be achieved over the entire process of the invention.

The second reaction step has been investigated thermodynamically and kinetically. Using data for the Gibbs Free Energies of Formation and the Enthalpies of the reactants and products shown in equation 2, the equilibrium constant was determined as a function of temperature. In this calculation, the assumption was made that only the ortho isomer of dichlorobenzene was present. The result is the following expression:

$$\log Kp = -880.7(1/T) + 7.67 \qquad 7.$$

where Kp is the equilibrium constant and T is the absolute temperature in degrees Kelvin. Using this equation, log Kp was calculated to equal 6.35 at 400° C. and 6.70 at 600° C. Thus, the equilibrium is extremely favorable for this reaction in the temperature range of 400° C. to about 700° C.

The reaction kinetics for equation 2 can be explained in terms of free radical reactions. This mechanism can be understood by the following equations:

$$C_6H_4Cl_2 \rightarrow C_6H_4Cl \cdot + Cl \cdot \qquad 8.$$

$$Cl \cdot + C_2H_6 \rightarrow C_2H_5 \cdot + HCl \qquad 9.$$

$$C_2H_5 \cdot + C_6H_4Cl_2 \rightarrow C_6H_4ClC_2H_5 + Cl \cdot \qquad 10.$$

In the above expression, the initiator of the free radical mechanism is shown by equation 8. The following two equations, numbers 9 and 10, constitute the chain reaction that is repeated over and over again. The speed by which the reactions in equations 9 and 10 occur determine the reaction kinetics, which is most favorable. When equations 9 and 10 are combined, the following relationship is obtained:

$$C_6H_4Cl_2 + C_2H_6 \rightarrow C_6H_4ClC_2H_5 + HCl \qquad 11.$$

The intermediate formed according to equation 11 above decomposes spontaneously and therefore rapidly to give styrene as follows:

$$C_6H_4ClC_2H_5 \rightarrow C_6H_5C_2H_3 + HCl \qquad 12.$$

By combining equations 11 and 12, the reaction in equation 2 is obtained.

Similar reasoning can be used to analyze the reaction in equation 5. By showing that chlorobenzene is an intermediate in the conversion of dichlorobenzene and ethane to styrene, it is possible to predict that equation 5 will go to completion. Likewise, the kinetics of equation 5 can be explained by using a model for the free radical reactions. The kinetics of both reactions represented by equations 2 and 5 are far superior to the cracking of ethylbenzene employed in the classical process for producing styrene. This result permits lower temperatures in the second reaction step of the present invention compared with the dehydrogenation conditions in the prior art. Thus, the formation of tars is reduced and superior yields are obtained.

Referring now to FIG. 1 in detail, R1 represents the catalytic reactor, R2 is the thermal reactor, S1 and S2 are phase separators, C1 and C2 are condensers, and D is a distillation column. In the embodiment shown, oxygen 1, recycled hydrogen chloride 4, benzene feed 2 and recycled benzene 3 are fed to R1. The effluent 10 from R1 is condensed in C1 and passed to S1 to remove water 7. The separated chlorobenzene and dichlorobenzene stream 5 along with ethane feed 6 are introduced to R2. The effluent 11 from R2 is condensed in C2 and then sent to S2 where hydrogen chloride 4 is separated from the crude product 8. The latter, comprising styrene and benzene is fed to D, which fractionates this stream to produce recycled benzene 3 and styrene product 9. The net result is the production of styrene 9 and by product water 7 from raw materials oxygen 1, benzene 2 and ethane 6.

The aromatic compound which is fed to the catalytic reactor in the process of this invention is any $C_{6-12}$ aromatic compound which is capable of being alkylated to an alkyl-substituted $C_{6-12}$ aromatic compound. Preferably, the $C_{6-12}$ aromatic compound is an unsubstituted or substituted benzene. More preferably, the $C_{6-12}$ aromatic compound is represented by the following formula:

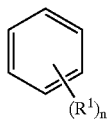

wherein n is an integer from 0 to about 3, and each $R^1$ is independently selected from the group consisting of hydrogen and $C_{1-5}$ alkyl moieties, more preferably, from methyl, ethyl, and propyl moieties, with the balance of the 6-n bonds being to hydrogen. Non-limiting examples of $C_{6-12}$ aromatic compounds which satisfy the above formula include benzene, toluene, xylenes, ethylbenzene, ethyltoluene, diethylbenzene, isopropylbenzene, and t-butylbenzene. Most preferably, the $C_{6-12}$ aromatic compound is benzene.

The alkane, which is fed to the thermal reactor, is any $C_{2-5}$ alkane which is capable of being dehydrogenated to the corresponding $C_{2-5}$ alkene. Suitable examples of $C_{2-5}$ alkanes include ethane, propane, n-butane, isobutene, and the various isomers of pentane. More preferably, the $C_{2-5}$ alkane is ethane or propane, and the corresponding $C_{2-5}$ alkene is ethylene or propylene. The reaction of the $C_{2-5}$ alkane with the chlorinated $C_{6-12}$ aromatic compound in the thermal reactor results in a $C_{2-5}$ alkane-substituted aromatic compound which preferably is represented by the formula:

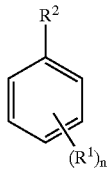

wherein n is an integer from 0 to about 3; each $R^1$ is independently selected from the group consisting of hydrogen and $C_{1-5}$ alkyl moieties; and $R^2$ is selected from $C_{2-5}$ alkyl moieties, with the balance of the 5-n bonds being to hydrogen. More preferred $C_{2-5}$ alkyl-substituted aromatic compounds consistent with the above formula include ethylbenzene, ethyltoluene, isopropylbenzene, diethylbenzene, and di(isopropyl)benzene. During the second reaction step, a spontaneous dehydrogenation occurs, $R^2$ is transformed from a $C_{2-5}$ alkyl moiety into a $C_{2-5}$ alkenyl moiety. The more preferred $C_{2-5}$ alkenyl-substituted aromatic products include styrene, α-methylstyrene, vinyltoluene, and divinylbenzene.

The present invention offers a process for the manufacture of styrene and other alkenyl-substituted aromatic compounds from less expensive raw materials, namely low molecular weight alkanes such as ethane. The novel process achieves higher yields of product and requires lower capital investment. With the advantages of the disclosed process, alkenyl-substituted aromatic compounds can be produced at significant savings in cost.

The following examples, whose sole purpose is to describe this invention in greater detail, should in no way be considered as limiting the scope of the invention.

An illustrative but non-limiting example is provided for a better understanding of the present invention and for its embodiment.

EXAMPLE 1

Engineering calculations were made to determine the yield of styrene produced from benzene by the present process. With reference to the flowsheet of FIG. 1, 100 lb. of benzene was fed to R1. Sufficient hydrogen chloride and oxygen were used to react 50% of the benzene so that 39.8% of the benzene feed was converted to chlorobenzene, 10.0% was converted to dichlorobenzene and 0.2% was lost due to combustion. (In U.S. Pat. No. 1,963,761 it was noted that "combustion of the benzene practically does not occur".) The resulting chlorinated benzenes were passed to R2 where they were pyrolyzed to give styrene, benzene and some tars. The efficiency of these reactions was assumed to be 98%. By recycling the unreacted benzene from R1 and the benzene formed in R2, 130 lb. of styrene was produced to give an overall conversion of 97.8%. This result compared favorable with conventional processes that are reported to achieve yields of 86 to 92%.

It will be apparent that the present invention has been described herein with reference to certain preferred or exemplary embodiments. The preferred or exemplary embodiments described herein may be modified, changed, added to, or deviated from without departing from the intent, spirit, and scope of the present invention.

What is claimed is:

1. An integrated process of preparing a $C_{2-5}$ alkenyl-substituted aromatic compound from a $C_{2-5}$ alkane and a $C_{6-12}$ aromatic compound, the process comprising:

(a) a first reaction step wherein a $C_{6-12}$ aromatic compound is reacted with hydrogen chloride to yield water and a chlorinated $C_{6-12}$ aromatic compound;

(b) a second reaction step wherein the chlorinated $C_{6-12}$ aromatic compound from the first reaction step is contacted with a $C_{2-5}$ alkane to produce a $C_{2-5}$ alkane-substituted aromatic compound that spontaneously dehydrogenates to a $C_{2-5}$ alkenyl-substituted aromatic compound and hydrogen chloride; and (c) separating the $C_{2-12}$ alkenyl-substituted aromatic compound from the hydrogen chloride, and any unreacted $C_{6-5}$ aromatic compounds.

2. The process of claim 1 wherein the $C_{2-5}$ alkane is selected from the group consisting of ethane, propane, and butanes.

3. The process of claim 2 wherein the $C_{2-5}$ alkane is ethane.

4. The process of claim 1 wherein the $C_{6-12}$ aromatic compound is represented by the formula:

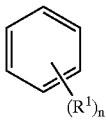

wherein n is an integer from 0 to about 3, and wherein each $R^1$ is independently selected from the group consisting of hydrogen and $C_{1-5}$ alkyl moieties, with the balance of the 6-n bonds being to hydrogen.

5. The process of claim 4 wherein the $C_{6-12}$ aromatic compound is benzene.

6. The process of claim 1 wherein the $C_{2-5}$ alkane-substituted aromatic compound is represented by the formula:

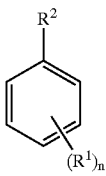

wherein n is an integer from 0 to about 3; each $R^1$ is independently selected from the group consisting of hydrogen and $C_{1-5}$ alkyl moieties; and $R^2$ is a $C_{2-5}$, alkyl moiety, with the balance of the 5-n bonds being to hydrogen.

7. The process of claim 1 wherein the $C_{2-5}$ alkane-substituted aromatic compound is selected from the group consisting of ethylbenzene, ethyltoluene, diethylbenzene, isopropylbenzene, and di(isopropyl)benzene.

8. The process of claim 1 wherein the first reaction step is performed in a fluidized bed reactor.

9. The process of claim 1 wherein the first reaction step is performed in a molten salt reactor.

10. The process of claim 1 wherein the first reaction step is catalyzed by copper chloride.

11. The process of claim 10 wherein the copper chloride catalyst is enhanced with metallic chlorides selected from the group consisting of: potassium, cesium, iron, cobalt, nickel, manganese, chromium, cerium, and lead.

12. The process of claim 1 wherein the first reaction step is catalyzed by a metal oxide.

13. The process of claim 1 wherein the first reaction step is carried out at a temperature between about 200° C. and 350° C.

14. The process of claim 1 wherein the second reaction step is carried out at a temperature between about 400° C. and 700° C.

15. An integrated process of preparing a $C_{2-5}$ alkenyl-substituted aromatic compound from a C2-5 alkane and a $C_{6-12}$ aromatic compound, the process comprising:
(a) a first reaction step wherein a $C_{6-12}$ aromatic compound is reacted with hydrogen chloride and oxygen in a catalytic reactor under process conditions sufficient to yield water and chlorinated $C_{6-12}$ aromatic compound;
(b) a second reaction step wherein the chlorinated $C_{6-12}$ aromatic compound from the first reaction step is contacted with a $C_{2-5}$ alkane to produce a $C_{2-5}$ alkane-substituted aromatic compound that spontaneously dehydrogenates to a $C_{2-5}$ alkenyl-substituted aromatic compound and hydrogen chloride;
(c) separating the $C_{2-5}$ alkenyl-substituted aromatic compound from the dehydrogenation effluent stream under conditions sufficient to obtain an essentially non-aromatic, gaseous stream comprising hydrogen chloride, and an aromatics stream comprising the $C_{2-5}$ alkenyl-substituted aromatic compound and unreacted $C_{6-12}$ aromatic compounds;
(d) recycling the hydrogen chloride generated in step (b) into the catalytic reactor of step (a); and
(e) recycling the unreacted $C_{6-12}$ aromatic compounds recovered from step (c) into the catalytic reactor of step (a).

16. The process of claim 15 wherein the $C_{2-5}$ alkane is selected from the group consisting of ethane, propane, and butanes.

17. The process of claim 16 wherein the $C_{2-5}$ alkane is ethane.

18. The process of claim 15 wherein the $C_{6-12}$ aromatic compound is represented by the formula:

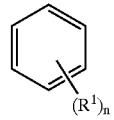

wherein n is an integer from 0 to about 3, and wherein each $R^1$ is independently selected from the group consisting of hydrogen and $C_{1-5}$ alkyl moieties, with the balance of the 6-n bonds being to hydrogen.

19. The process of claim 18 wherein the $C_{6-12}$ aromatic compound is benzene.

20. The process of claim 15 wherein the $C_{2-5}$ alkane-substituted aromatic compound is represented by the formula:

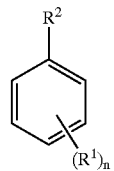

wherein n is an integer from 0 to about 3; each $R^1$ is independently selected from the group consisting of hydrogen and $C_{1-5}$ alkyl moieties; and $R^2$ is a $C_{2-5}$, alkyl moiety, with the balance of the 5-n bonds being to hydrogen.

21. The process of claim 15 wherein the $C_{2-5}$ allkane-substituted aromatic compound is selected from the group consisting of ethylbenzene, ethyltoluene, diethylbenzene, isopropylbenzene, and di(isopropyl)benzene.

22. The process of claim 15 wherein the dehydrogenation reactor comprises a fluidized bed reactor.

23. The process of claim 15 wherein the dehydrogenation reactor comprises a molten salt reactor.

24. The process of claim 15 wherein the catalytic reactor contains copper chloride as catalyst.

25. The process of claim 24 wherein the copper chloride catalyst is enhanced with metallic chlorides selected from the group consisting of: potassium, cesium, iron, cobalt, nickel, manganese, chromium, cerium, and lead.

26. The process of claim 15 wherein the catalytic reactor contains a metal oxide.

27. The process of claim 15 wherein the first reaction step is carried out at a temperature between about 200° C. and 350° C.

28. The process of claim 15 wherein the second reaction step is carried out at a temperature between about 400° C. and 700° C.

29. An integrated process of preparing styrene from ethane and benzene, the process comprising:
  (a) a first reaction step wherein benzene is reacted with hydrogen chloride and oxygen in a catalytic reactor under process conditions sufficient to yield water and chlorinated benzene;
  (b) a second reaction step wherein the chlorinated benzene from the first reaction step is contacted with ethane under process conditions sufficient to produce styrene and hydrogen chloride; and
  (c) separating the styrene from hydrogen chloride and any unreacted benzene.

30. The process of claim 29 wherein hydrogen chloride generated in step (b) is recycled into the catalytic reactor of step (a).

31. The process of claim 30 wherein unreacted benzene recovered from step (c) is recycled into the catalytic reactor of step (a).

32. The process of claim 29 wherein the first reaction step is performed in a fluidized bed reactor.

33. The process of claim 29 wherein the first reaction step is performed in a molten salt reactor.

34. The process of claim 29 wherein the first reaction step is catalyzed by copper chloride.

35. The process of claim 34 wherein the copper chloride catalyst is enhanced with metallic chlorides selected from the group consisting of potassium, cesium, iron, cobalt, nickel, manganese, chromium, cerium, and lead.

36. The process of claim 29 wherein the first reaction step is catalyzed by a metal oxide.

37. The process of claim 29 wherein the first reaction step is carried out at a temperature between about 200° C. and 350° C.

38. The process of claim 29 wherein the second reaction step is carried out at a temperature between about 400° C. and 700° C.

* * * * *

UNITED STATES PATENT AND TRADEMARK OFFICE
CERTIFICATE OF CORRECTION

PATENT NO. : 6,852,896 B2
DATED : February 8, 2005
INVENTOR(S) : John E. Stauffer It is certified that error appears in the above-identified patent and that said Letters Patent is hereby corrected as shown below:

Column 3,
Line 43, please change equation 6 to read as follows:
-- $C_6H_3Cl_3 + C_6H_5Cl + 2\ C_2H_6 \rightarrow 2\ C_6H_5C_2H_3 + 4\ HCl$ --

Signed and Sealed this

Twenty-fourth Day of May, 2005

JON W. DUDAS
*Director of the United States Patent and Trademark Office*